United States Patent
Tverskoy et al.

[11] Patent Number: 6,117,103
[45] Date of Patent: Sep. 12, 2000

[54] INFUSION APPARATUS

[75] Inventors: Grigory N. Tverskoy; Leonid Lipetsker, both of Arad; Evgeny Voronov, Beer-Sheeva; Roman Struzer, Arad, all of Israel

[73] Assignee: Medun Ltd., Arad, Israel

[21] Appl. No.: 09/202,102

[22] PCT Filed: Jun. 30, 1997

[86] PCT No.: PCT/IL97/00218

§ 371 Date: Jun. 10, 1999

§ 102(e) Date: Jun. 10, 1999

[87] PCT Pub. No.: WO98/00186

PCT Pub. Date: Jan. 8, 1998

[30] Foreign Application Priority Data

Jul. 1, 1996 [IL] Israel ........................................ 118766

[51] Int. Cl.[7] .................................................. A61M 57/00
[52] U.S. Cl. ..................... 604/82; 604/250; 128/DIG. 13
[58] Field of Search ................................. 604/250, 153, 604/154, 80, 81, 82, 83, 246, 259, 151; 128/DIG. 12, DIG. 13; 222/134–137, 145.7; 417/118, 120, 16

[56] References Cited

U.S. PATENT DOCUMENTS

| | | |
|---|---|---|
| 3,550,619 | 12/1970 | Halasz . |
| 4,559,036 | 12/1985 | Wunsch .............................. 604/250 X |
| 4,673,390 | 6/1987 | Archibald .................................. 604/81 |
| 4,696,671 | 9/1987 | Epstein et al. . |
| 5,378,231 | 1/1995 | Johnson et al. . |
| 5,423,749 | 6/1995 | Merte et al. ........................ 604/250 X |

FOREIGN PATENT DOCUMENTS

| | | |
|---|---|---|
| 0 013 334 A2 | 12/1979 | European Pat. Off. . |
| 473240 | 8/1988 | European Pat. Off. . |
| 295 16546 | 10/1995 | Germany . |
| WO 93/12825 | 7/1993 | WIPO . |

*Primary Examiner*—Wynn Wood Coggins
*Assistant Examiner*—A. T. Nguyen
*Attorney, Agent, or Firm*—Cowan, Liebowitz & Latman, P.C.; William H. Dippert

[57] ABSTRACT

A multi-drug intravenous infusion apparatus which comprises a plurality of vials containing drugs to be provided to a patient; a fluid container containing fluid to be mixed with the drugs; conduit mechanism for leading drugs from the vials, mixed with the fluid from the container, to mechanism for introducing the drugs with the fluid into the patient's body, the conduit mechanism comprising: a main section, a plurality of individual sections, each comprising at least a collapsible portion, connected to the vials and to the main sections, a terminal section connected to the main section and the mechanism for introducing the drugs with the fluid into the patient's body, and a fluid section leading fluid from the fluid container to the terminal section; a switching unit comprising a plurality of switches, each one associated with one of the individual sections, wherein each switch is capable of either blocking the drug flow in the associated section by exerting pressure whereby to collapse the collapsible portion thereof or allowing the flow by releasing the collapsible portion; and a programmable processor for managing and regulating the operations of the switching unit.

22 Claims, 6 Drawing Sheets

CHANNEL I OPENED

| CHAN. N° POS | I | II | III | IV |
|---|---|---|---|---|
| 1 | 1 | 0 | 0 | 0 |
| 2 | 0 | 1 | 0 | 0 |
| 3 | 0 | 0 | 1 | 0 |
| 4 | 0 | 0 | 0 | 1 |
| 5 | 1 | 0 | 1 | 0 |
| 6 | 1 | 0 | 0 | 1 |

1 - OPENED
0 - CLOSED

CHANNEL II CLOSED

CHANNEL III CLOSED

CHANNEL IV CLOSED

INFUSION APPARATUS

FIELD OF THE INVENTION

The invention relates to medical devices. More particularly, the invention relates to an improved apparatus for infusing a plurality of drug dosages to a patient.

BACKGROUND OF THE INVENTION

Apparatuses for intravenously infusing drugs to a patient are well known and heavily used during many medical procedures. Infusion apparatuses are characterized by having at least one drug dosage in a container, pumping means, a liquid conduit for conveying a stream of liquid from the container to the vein, and means for penetrating the body and injecting the drug into the vein. An additional fluid container is provided, to hold the fluid which is mixed with the drug and carries the drug to the vein. Apparatuses for timely supplying one of a plurality of drugs to a patient are also known, and such apparatuses are normally provided with a microcontroller for controlling the operation of the device, and with display and keyboard means for programming the apparatus in order to perform the desired sequence of operations with the desired timing. Further, a system for centrally controlling a plurality of infusion apparatuses has lately been developed. Such systems enable a member of the medical personnel to simultaneously manage and control the proper operation of several infusion apparatuses, wherein each particular apparatus can be separately programmed for timely providing one or more of a plurality of different drug dosages to a patient. The system includes a data connection such as by a data bus or a serial connection between a plurality of apparatuses and between them and a central PC. The programming of the system can be carried out either locally in each apparatus, or centrally by the personnel controller at the main PC.

An infusion apparatus for timely providing one of a plurality of drug dosages to a patient is disclosed in U.S. Pat. No. 5,317,506, and schematically shown in FIG. 1. The apparatus comprises a processor 1 for regulating the operation of the apparatus, and a plurality (normally up to 5) of drug vials 10. Each particular drug vial is connected to its dedicated infusion pump 21, and each pump outlet 8 is coupled to a main conduit 6. The main conduit 6 may, in some cases, be included within a component known as a "connector". Said connector has a plurality of individual fluid input ports, all leading to one main channel, which in turn leads to one fluid output port. Throughout the invention it should be understood that whenever the term "connector" is used, it refers to a component which routes fluid from plurality of input ports each one connected to a fluid channel, to one output channel. The main conduit 6 delivers the selected drug to the patient, mixed with fluid coming from fluid container 7, via conduit 9. In said apparatus each infusion pump is controlled by the main processor 1, and is independently operable to infuse a medication into the vein of the patient in accordance with a programmed procedure. Means are also provided for enabling the operation of only one infusion pump at any given time. The said apparatus suffers from a major drawback, viz. it requires the use of a separate infusion pump for each particular drug channel (the term "drug channel", when used herein, refers to a path followed by a drug from a particular drug vial to the patient). Hence, the apparatus is relatively complex, cumbersome and expensive.

U.S. Pat. Nos. 5,378,231 and 4,696,671 disclose another type of n-channel, programmable drug and fluid delivery apparatus, which comprises an Infusion Pump Unit (hereinafter referred to also as IPU). The IPU accommodates a plurality of disposable pumping cassettes 44, each cassette serving one drug channel. The cassettes (best described in U.S. Pat. No. 4,696,671), which are complicated in their structure and relatively expensive, should be replaced and disposed of when connecting the infusion apparatus to a new patient, or periodically for the same patient. Further, each cassette requires for its operation dedicated motor means and driver means, and therefore, a plurality of motors and drivers are required. The apparatus, as shown in FIG. 2, comprises a plurality of drug vials 10 and one fluid container 7. While operative, the apparatus infuses at a predetermined time one selected drug, mixed with fluid from container 7, to the patient. The apparatus has n pumping channels 4, wherein each channel operates independently, and is controlled and concurrently monitored by processor (PC) 1. The main conduit 16 of the apparatus may be connected to a manifold or directly to the patient. As shown, the apparatus comprises only one IPU, having a plurality of pumping cassettes 44. Each cassette within the drug channel can be accessed (e.g., in U.S. Pat. No. 5,378,231) by lifting a protective hood. While in use, it is recommended that the hood be locked in order not to interrupt the proper operation of the device and to prevent removal of drugs. However, each pumping cassette is activated by a motor which is attached to gear means for reducing the motor revolutions, and each particular motor is driven by a dedicated driver. Therefore, the apparatus of FIG. 2 requires a plurality of motors, drivers and gear means. Further, sterility considerations require the frequent replacement of the relatively expensive cassettes, connector (when available), and conduits. Hence, the apparatus is cumbersome, costly, and requires frequent and complicated service for its operation.

It should be noted here that current regulations in essentially all countries require the disposal of a complete infusion set to obtain a new one, for any new patient. An infusion set consists of all the parts that are in direct contact with the fluid infused to the patient. In the apparatus of FIG. 1, those parts are the drug vials, connector and the conduits. In the apparatus of FIG. 2, the administration set consists of the drug vials, the conduits, the cassettes and connector (when exists).

It is an object of the invention to provide a multi-channel apparatus for providing infusion of several medications to a patient, which does not suffer from the abovementioned drawbacks.

It is another object of the invention to provide an infusion apparatus which is more reliable and of lower cost.

It is a further object of the invention to provide an apparatus which is much easier to serve, program, and maintain from the prior art ones.

It is still a further object of the invention to eliminate the cost and time consumption involved in the replacement of disposable elements which are part of each administration set, and more particularly, to eliminate the use of a disposable cassette as an essential part of each infusion channel.

SUMMARY OF THE INVENTION

The invention relates to a multi-drug intravenous infusion apparatus, said apparatus comprising a plurality of vials containing drugs to be provided to a patient, a fluid container containing a fluid to be mixed with said drugs, conduit means for leading drugs from said vials, mixed with fluid from said container to the patient, said conduit means comprised of the following sections:

a. a main section;

b. a plurality of individual sections, each comprising at least a collapsible portion, connected to said vials and to said main section;

c. a terminal section connected to said main section and to means for introducing the drugs with said fluid into the patient's body; and d. a fluid section leading fluid from said fluid container to said terminal section.

Said conduit means can be made of one integral piece or of more than one piece.

The apparatus further comprises an infusion pump for causing the drug to flow from said vials to said introducing means, a switching unit comprising a plurality of switches, each one associated with one of said individual sections, wherein each switch is capable of either blocking the drug flow in the associated section by exerting pressure on and collapsing the same, or allowing said flow by releasing said associated section; and a programmable control means for managing and regulating the operation of the apparatus. Normally, it is preferable to inject only one drug into a patient at any given time; however, the apparatus can be easily programmed to mix more than one drug, taken from two or more of said vials at a given time, and to provide the same to the patient.

According to a preferred embodiment of the invention, the infusion pump is a peristaltic infusion pump acting on the outer surface of the terminal section of the conduit. According to another embodiment of the invention, the infusion pump is a cassette infusion pump. Alternatively, the apparatus can include no pump at all, and drug flow can be effected by force of gravity caused by the weight of the drugs contained in the drug vials.

According to a preferred embodiment of the invention, each switch of the switching unit comprises a rigid means for contacting a flexible portion of one of the individual sections of the conduit means, and means for selectively displacing said rigid means towards said flexible portion of said individual section in order to collapse it and block the drug flow, or moving it away from said flexible portion for releasing the same and allowing the drug flow. The means for displacing the rigid means according to the invention can be of various known types, such as an eccentric disc or an electromagnet.

According to another embodiment of the invention, each switch of the switching unit comprises an eccentric disc directly contacting a flexible portion of one of the individual sections of the conduit means, and said eccentric disc, depending on its angular position with respect to said section, either blocking the drug flow in the associated section by collapsing the same, or allowing drug flow by releasing said section.

The switching unit of the apparatus according to the invention comprises:

a. At least two eccentric rotatable discs spaced apart on one shaft;

b. Means such as a motor for rotating said shaft;

c. For each eccentric disc, a body contacting the perimeter of said disc and displaceable by the rotation of said disc towards an individual conduit section to apply pressure to the outer surface thereof, whereby to collapse the same, or being allowed to become displaced away from said conduit whereby to release the same, in order to block or permit flow in it respectively;

d. each disc having at least two angular positions, in one of which it displaces said displaceable body towards said conduit section, while in the other it allows it to be displaced away from it.

Hereinafter, when a switch is in a position in which it collapses the associated conduit section, it may be said that it is in an "open" state, while when it is in a position in which it releases the associated conduit section, it may be said that it is in a "closed" state, When the switch comprises an eccentric disc, an "open" state is defined by an angular position in which the disc contacts a displaceable body or said conduit section, as the case may be, with a portion of its perimeter in which the radius of the disc is minimal, and a "closed" state is defined by an angular position in which the disc contacts a displaceable body or said conduit section, as the case may be, with a portion of its perimeter in which the radius of the disc is maximal.

According to one embodiment of the invention, each eccentric disc defines two states, i.e., "closed" and "open" states. According to another embodiment of the invention, each eccentric disc, while rotating over its full perimeter, changes more than twice between "closed" and "open" states. Optionally, the apparatus may include one or more position sensors for providing to the control means the current state of the motor, and/or of the eccentric discs.

Preferably, the control means according to the invention is a local processor comprising a timer and keyboard and display means for programming the apparatus to timely perform tasks. More preferably, according to the invention means are also provided for connecting the apparatus to other infusion apparatuses, and/or to a central control unit which controls plurality of infusion apparatuses.

The invention also relates to method for infusing drugs to a patient wherein means are provided for either exerting pressure on the outer surface of one or more flexible conduits carrying drugs to a patient in order to block the fluid flow in said conduits, or for releasing the pressure exerted on said one or more flexible conduits in order to allow fluid flow in said one or more flexible conduits. Said means in conjunction with a peristaltic infusion pump provides a full sterility infusion apparatus wherein replacement of only the conduits and vials is required.

DETAILED DESCRIPTION OF PREFERRED EMBODIMENTS

Figure 1:
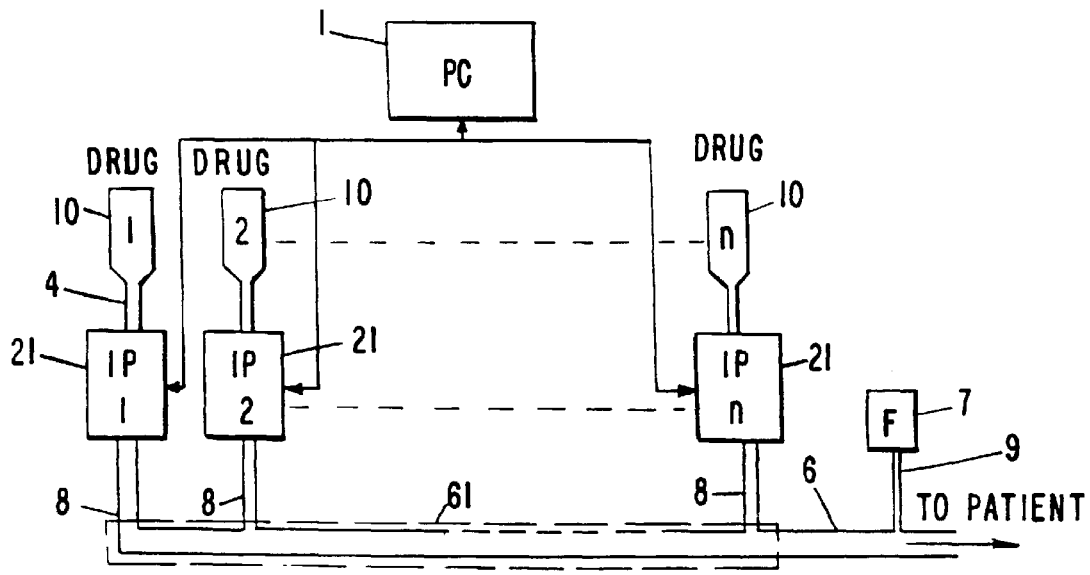
FIG. 1 shows in block diagram a multi-channel infusion apparatus of the prior art.
Figure 2:
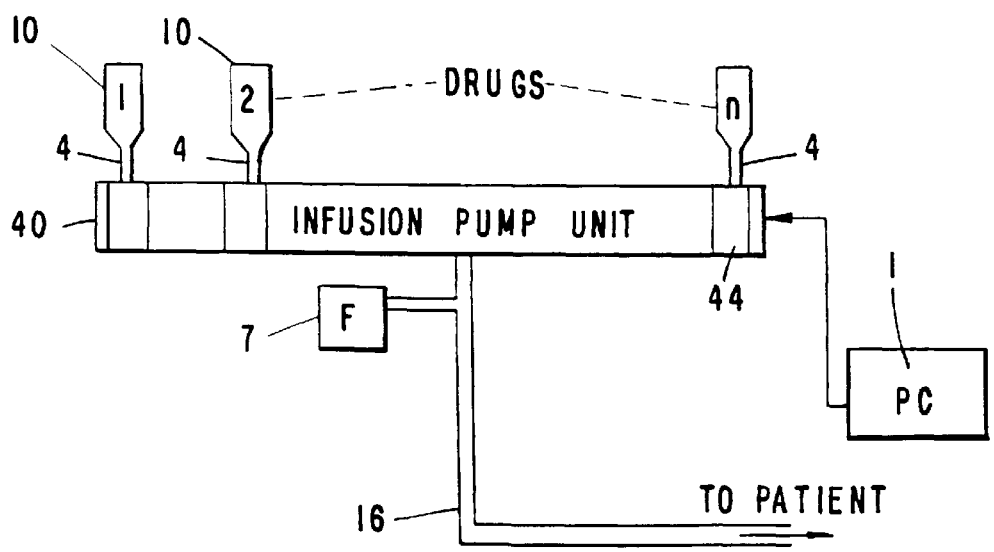
FIG. 2 schematically shows another version of a multi-channel infusion of the prior art.
Figure 3:
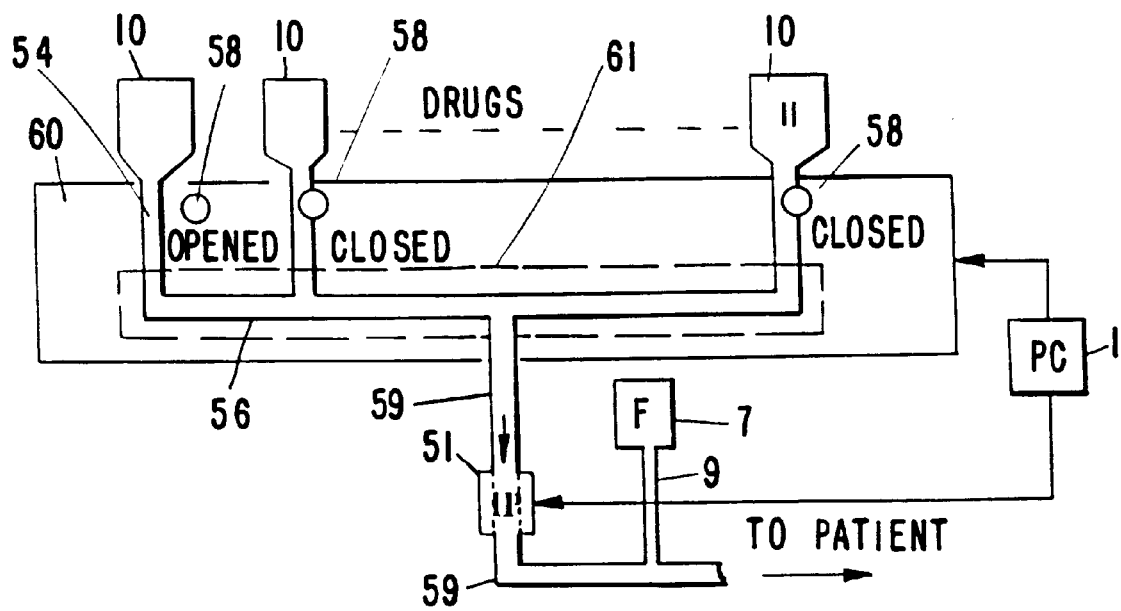
FIG. 3 shows in block diagram the basic structure of a multi-channel infusion apparatus, according to one embodiment of the invention.

FIG. 3 schematically describes an infusion apparatus according to a preferred embodiment of the invention. The apparatus comprises a plurality (n) of drug vials 10 containing drugs to be injected at predetermined times to a patient. Conduit means are provided for allowing the transfer of drugs from said drug vials to the patient. Said conduit means comprises a plurality of individual sections, a main section, a terminal section, and a fluid section. The individual sections of the conduit means comprise n individual tubes 54 which connect between each one of said n drug vials 10 and a main section 56 as shown. The main section 56, may be a part of a connector 61. Hereinafter, when the term "main section" is referred to, it should be understood that this section may be a part of, or contained within, a connector. A terminal section 59 leads drugs from said main section 56, and through infusion pump 51, to the means for introducing the drugs to the body of the patient. Said terminal section is connectable in any convenient way to said introducing means, which may be conventional, such as an infusion needle, not shown, for penetrating the patient's blood vessels. Normally, it is highly preferable that the individual sections 54, the main section 56, terminal section 59, and the fluid section be made of a single conduit member, as this member has to be used for only one patient and later discarded. However, in some applications this member can be made of more than one piece.

Switching unit 60, containing a plurality (n) of switches, schematically indicated as 58, provides control over the drug flow in each one of individual sections 54. Each one of said switches 58 can either allow drug flow in one respective individual section 54, or block such flow. Processor (PC) 1, controls the operation of the switching unit 60, and in predetermined times activates one of said switches 58, and deactivates the rest (n−1) of the switches 58. As mentioned, in some cases connector 61 may be used to route drugs from the individual sections 54 to the main section, and through the main section 56 to the terminal section 59. A single infusion pump 51, effects drug flow from one of the drug vials 10, through one individual section 54, through the main section 56 and terminal section 59, to the patient. The flowing drug is mixed on its way to the patient with fluid F from container 7 flowing in section 9. It is preferable to use a peristaltic infusion pump in conjunction with the apparatus, in order to achieve full sterility, as such a pump acts on the outer surface of the conduit. A common peristaltic pump comprises a first advancing roller which occludes the conduit, which as it recovers to its normal size, draws in fluid which is then trapped by a second roller which advances the fluid out of the pump. Therefore, the pump does not contaminate the fluid, and the fluid does not contaminate the pump, and no replacement of any pump component is needed in order to maintain sterility. Another alternative, although not preferable, is to use in conjunction with the apparatus a cassette pump, known in the art, wherein the cassette has to be discarded and replaced for each patient. Another drawback of using this type of infusion pump is the need to cut the section 59 in two, or to use two sections, wherein one section is connected to the input of the pump and the other one to the output of the pump. Therefore, using this type of pump is more cumbersome, although possible. The following discussion, if not otherwise specifically stated, relates to the case in which a peristaltic infusion pump is used.

It should also be noted that all use of a pump within the apparatus is optional, as it is possible to effect drug flow in the conduits by exploiting the force of gravity caused by the weight of the drugs contained in the drug vials. As mentioned, the switching unit 60 of the apparatus comprises plurality (n) of switches indicated as 58. Each one of said switches can either block the drug flow in the corresponding section by exerting a pressure on its outer surface and collapsing a segment of it, or enable a flow by not exerting said pressure. Of course, the conduits must be flexible and collapsible in at least the points of contact with the switches 58, and in the point of contact with the peristaltic infusion pump 51. In the drawings, a dark circle symbolizes a closed switch (viz., a closed drug path) and a white circle symbolizes an open switch (viz. an open path). Means are also provided for activating one switch and deactivating the rest (n−1) of the switches, in order to allow at any given time a delivery of only a single drug from a selected drug vial 10 to the patient. The closing and opening of the plurality of drug paths are carried out in a totally sterile manner, because the switches act on the outer surface of the individual conduits. Also, as schematically shown in FIG. 3, the infusion pump 51 or any part of the apparatus cannot be contaminated by drugs or by any other fluid flowing in section 59, and also the pump cannot contaminate the flowing fluids, as full insulation is kept between the pump and the fluids in any section of the conduit means. Particularly, when a peristaltic pump is used, the use of expensive disposable cassettes associated with complicated drivers, as well as the need for frequent replacement of cassettes when connecting the apparatus to a new patient, is eliminated. In the infusion apparatus according to the invention, only the drug vials and the conduit means, the cost of which is negligible, require replacement. Also, the apparatus comprises only one infusion pump 51, and therefore its complication is significantly reduced. The apparatus is also of lower cost, is more reliable, and easier to maintain and service.

Figure 4:
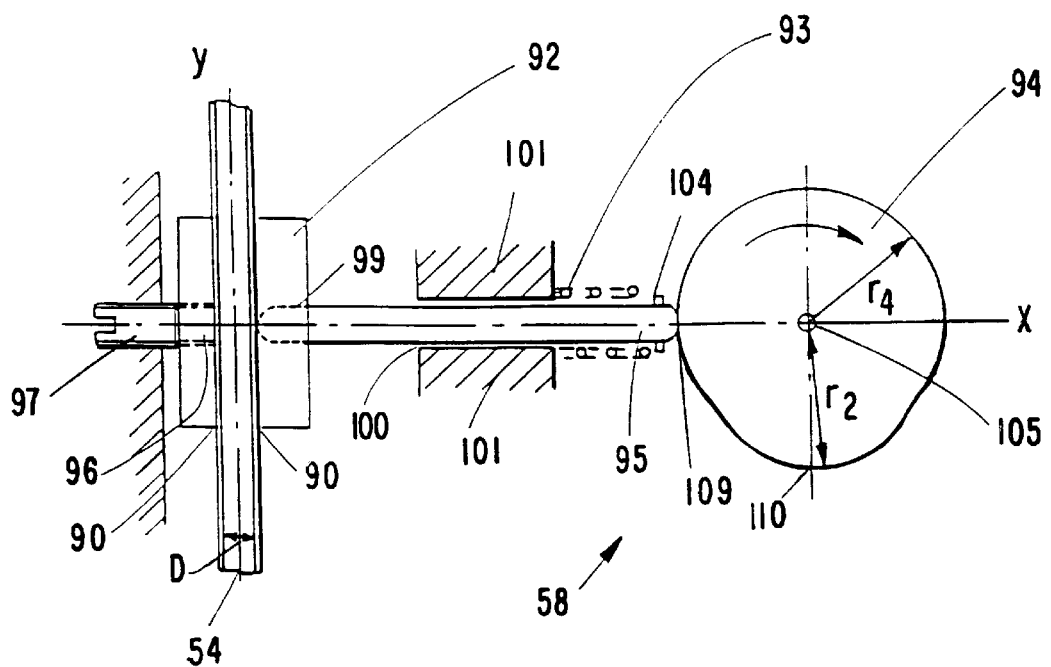
FIG. 4 illustrates a switch for either allowing or blocking the drug flow by the application or release of pressure on the external surface of a flexible conduit carrying drug to a patient, according to one embodiment of the invention.
Figure 5:
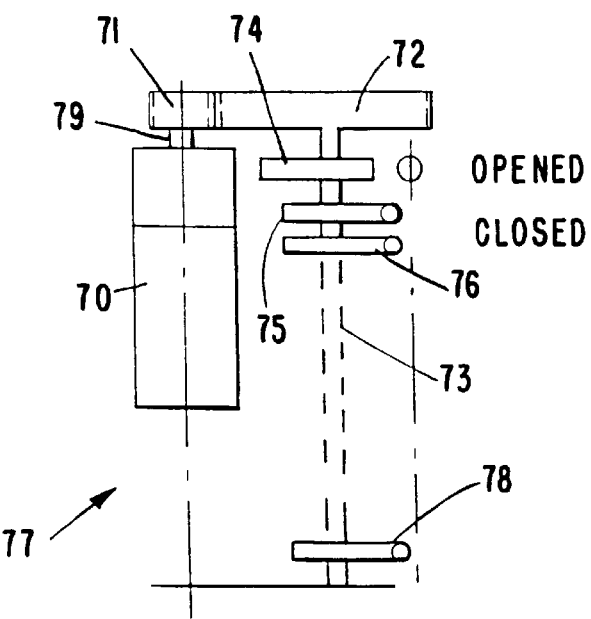
FIG. 5 illustrates a mechanical structure for activating a plurality of switches of the type shown in FIG. 4, according to one embodiment of the invention.

FIG. 4 illustrates the mechanical structure of a switch according to one embodiment of the invention. As said, each particular switch 58 (in FIG. 3) has two states. When the switch is in an inoperative state (hereinafter referred to as an "open" state), it allows drug flow through a drug conduit, and when in the operative state (hereinafter referred to as "closed" state) it blocks such flow. The switch comprises a base 92 having a passage 90, which is adapted to accommodate a flexible portion of a conduit section 54, and a bore 99, which is adapted to accommodate a pin 95. The axis of said pin is designated hereinafter as "X axis". Preferably, the bore 99 in said base 92 is created along that axis, perpendicular to said portion of section 54 carrying drug to the patient. A support 101, partially illustrated, is provided slidably to support pin 95, passing through bore 100 in support 101, contacts at one end the outer surface of eccentric disc 94 and at the other end the outer surface of flexible drug conduit 54. Tension spring 93 which bears at one end on retaining means attached to pin 95, e.g., on a small pin 104, and bears on at its other end on support 101, urges pin 95 towards eccentric disc 94 along X axis in the right-hand direction (as seen in FIG. 5) in order to assure a continuous contact between pin 95 and eccentric 94. As shown, eccentric 94, which rotates about shaft 105, has two radiuses $r_1$ and $r_2$ wherein $r_1 \neq r_2$. The term radius, when used herein, indicates to the distance from the center of the shaft 105 to a point along the outer surface of the disc, and does not imply that the periphery of the disc must be constituted by arcs of circles. The difference between said two radiuses should be equal to the inner diameter of conduit 54, i.e., $r_2 - r_1 = D$. When the disc 94 is in the angular position shown in FIG. 4, and pin 95 is in the rightmost position, there is an open drug path in conduit 54 and the switch herein described is in the "open" state. The rotation of disc 94 from the position illustrated in FIG. 5 to a position wherein pin 95 contacts disc 94 at point 110 (vis. the point on the outer surface of the disc where the radius is $r_2$), pushes pin 95 to the left (as seen in FIG. 4), and the pin collapses conduit 54 and blocks the drug flow in it. The switch herein described is thus in its "closed" state. It is clear that there is no contact between pin 95 or any element of the switch and the drug flowing in section 54, and therefore contamination of any type is eliminated. Further, although the use of eccentric discs is preferable, the movement of pin 95 to the right or left can be obtained by other means, such as by electromagnets, or by other means easily devised by skilled persons within the scope of the invention. Fastening screw 97 passing through threaded bore 96 enables the adaptation of the apparatus to conduit sections of different diameters. Furthermore, according to another embodiment of the invention the switch will be structured such that the eccentric disc itself be in contact with a portion of section 94, and the disc itself will exert directly a pressure on said portion of section 54 or release the same in order to permit or prevent flow accordingly.

FIG. 5 shows in schematic form a basic mechanical structure of a switching unit containing a plurality of switches of the type depicted in FIG. 4. The switching unit 77 comprises a single motor 70 having a shaft 79 to which is keyed a first gear 71, which in turn meshes with a second gear 72. This latter is keyed to shaft 73. A number (n) of eccentric discs 74, 75, 76, and 78, axially spaced over shaft 73, are keyed to said shaft. Each of said discs is part of a switch such as illustrated in FIG. 4. The motor 70 rotates shaft 73 and eccentric discs 74, 75, 76, and 78 to one of several defined angular positions. The eccentric discs are mounted on shaft 73 in staggered angular relationship to it, in such a manner that, in each particular angular position of the shaft, all but one of the switches comprising said eccentric discs are in the closed state, and only one of them is positioned in the open state. Generally, it is preferred that only one switch be in the open state at any moment, but this is not necessary, and there may be cases in which it will be desired to simultaneously place more than one switch in the open state, as will be further explained hereinafter.

FIG. 5 shows one phase of motor 70 in which only the uppermost eccentric disc 74 is in the open state, and all the remaining eccentric discs are in the closed state. Therefore, drug flows through the channel 54 with which eccentric disc 74 is associated, but the drug flow through all the remaining channels is blocked. It is of course possible to provide a state of all-closed channels by angularly positioning the discs over shaft 73 accordingly. Further, according to the invention the motor can rotate shaft 72 in only one direction (clockwise or counterclockwise) or in both directions when desired. It should also be noted that there may be cases in which a need will arise concurrently to provide a mixture of two or more drugs to a patient.

Figure 6A:
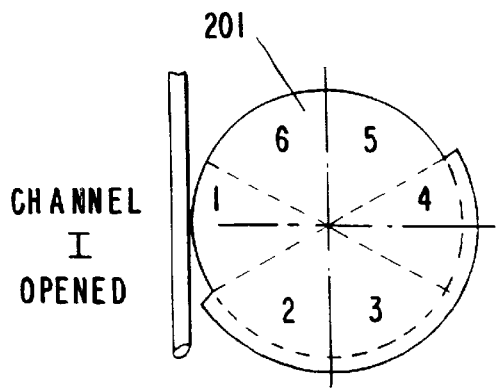
FIGS. 6a and FIG. 6b show two possible states of a multi-channel apparatus according to the invention.
Figure 6A:
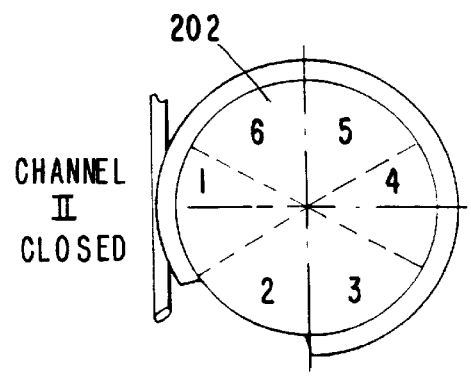
Figure 6A:
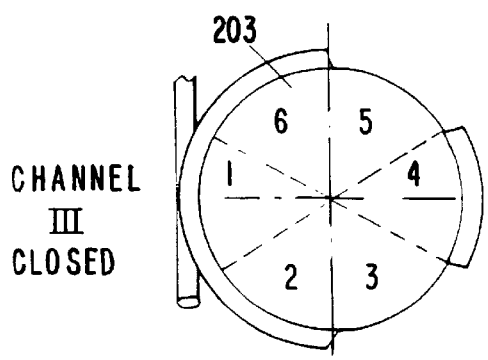
Figure 6A:
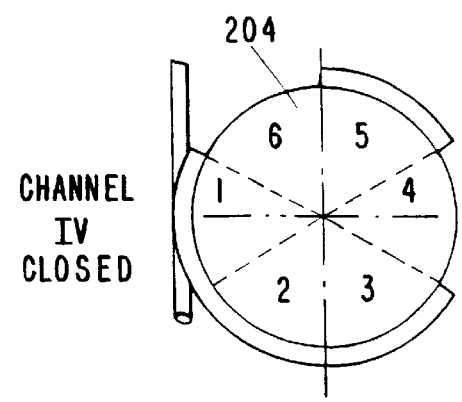
Figure 6B:
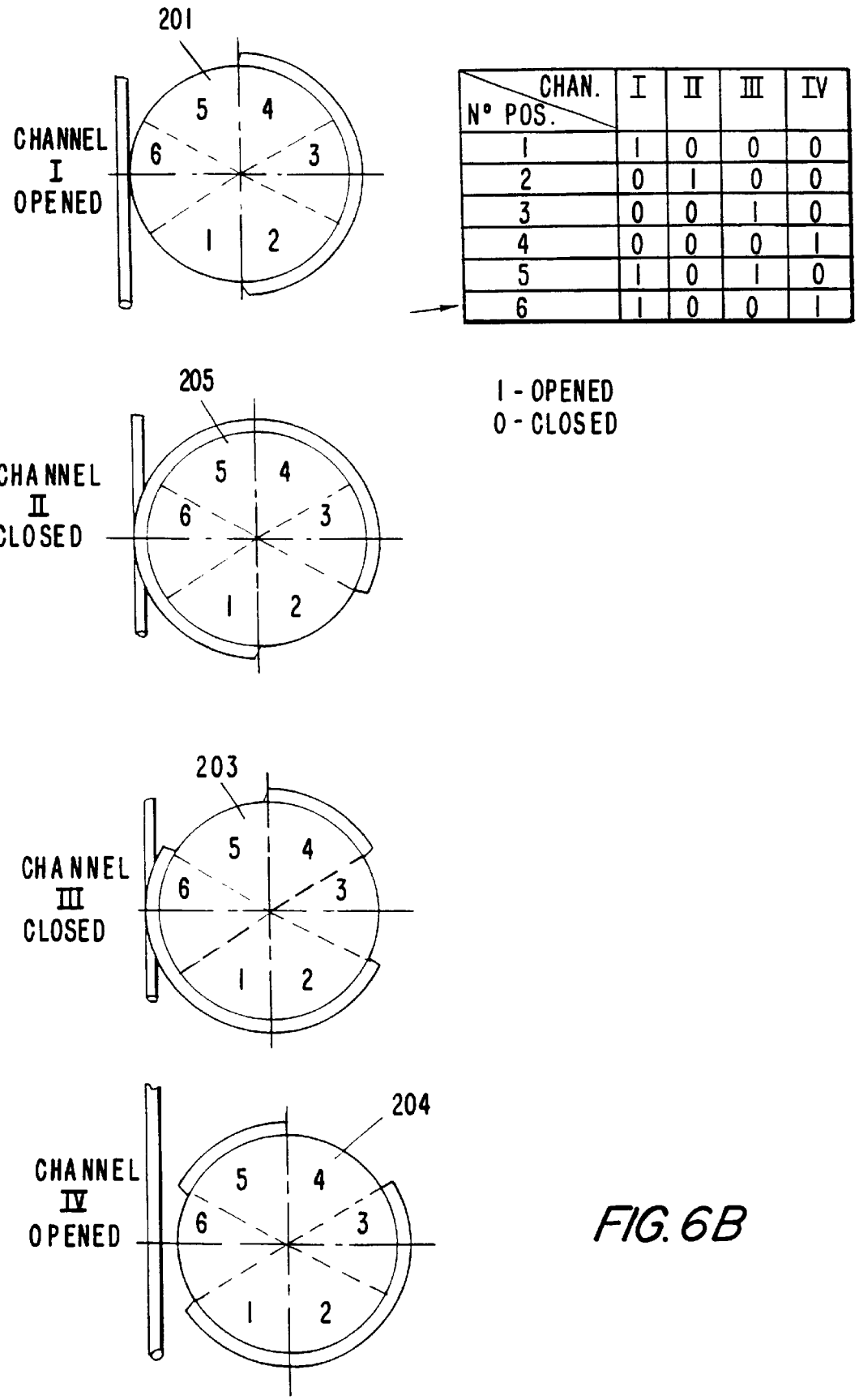

FIGS. 6a and 6b show two embodiments of the invention, wherein the apparatus comprises 4 drug channels, associated with eccentric discs 201, 202, 203, 204. Each disc has 6 possible angular positions indicated by numerals 1 to 6. FIGS. 6a and 6b are schematic and do not show the switches in their entirety, as does FIG. 4, but show only the eccentrics and the associated channels in order to evidence the position in which these latter are open or closed. FIG. 6a shows an angular position of the shaft wherein one disc 201, causes one channel (channel I) to be open and the three remaining discs 202, 203 and 204 cause the associated channels (channels II, III and IV) to be closed. The table enclosed in FIG. 6a lists in the first column the angular positions of the discs (and therefore of shaft 73) numbered 1 to 6, and in the remaining four columns the conditions of the four channels in each of the four angular positions, "1" indicating an open channel and "0" a closed channel. In FIG. 6a the angular position of the shaft 73 is position 1. FIG. 6b shows all angular position of the shaft 73 (position 6) wherein two discs 201 and 204 provide open channels (channels I and IV) and two discs 202 and 203 provide closed channels (channels II and III).

The apparatus according to the invention also comprises control means such as a microcontroller or a microprocessor of any type or form known in the art, for controlling its operation. The apparatus, of course, also includes known means for driving the motor in the desired manner, and keyboard and display means of any type known in the art. These means will not be described here for the sake of brevity, as they are well known in the art. Further, according to the invention, the apparatus may comprise a button for manually advancing the motor in order to ease the replacement of the drug vials and conduits. Pushing of the button will position the shaft into an angular position where one channel is "open", and therefore there is no collapsing of the individual section relating to that channel. A further push will release collapsing of another individual section, and so on. Therefore, sequential push of the button will enable release of the conduits from the apparatus for replacement, each one in its turn.

It should be noted here that there are several possible options in which the control means, such as the microcontroller, the keyboard, and the display can be physically positioned, or according to which the switching unit can be controlled. According to a first option, the control over the switching unit can be made from an external PC. In this case, the switching unit will not necessarily comprise a microcontroller and/or a keyboard and display. According to a second option, the control over the switching unit is made by a microcontroller which is encased within the housing of the switching unit. In this option, the switching unit should include a microcontroller, keyboard and display. According to a third option, the control over the switching unit is made by a microcontroller which is encased within the housing of the infusion pump. In this case also, the switching unit will not necessarily comprise a microcontroller and/or a keyboard and display. According to a fourth option, when the apparatus does not comprise an infusion pump, and the drug flow is carried out by the force of gravity, the control over the switching unit may be made either by a microcontroller which is encased within the housing of the switching unit or by an external PC as hereinbefore mentioned.

Figure 7:
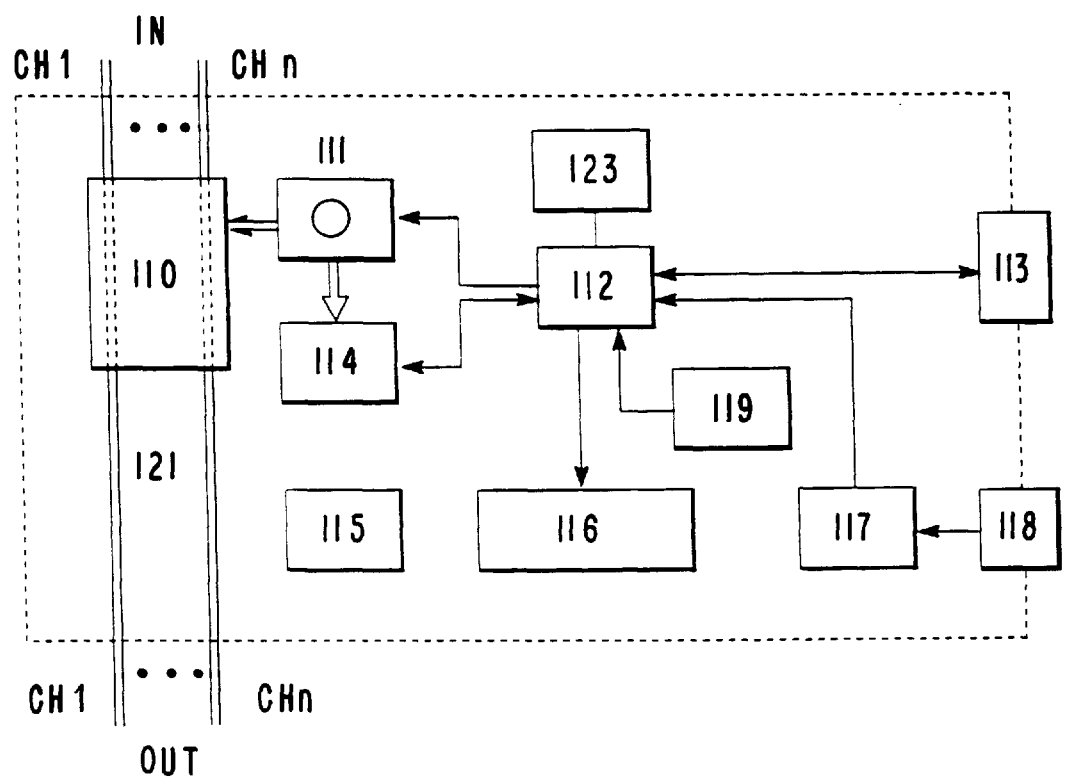
FIG. 7 shows in block diagram form the structure of a multi-channel switching unit according to one embodiment of the invention.

FIG. 7 shows another block diagram of the switching unit according to one embodiment of the invention. As shown, the apparatus comprises n channels for infusing drugs to a patient. The distinct n conduits 121 pass through a plurality of switches 110, activated by a motor 111. Position sensors 114 indicate to microprocessor or microcontroller 112 the current state of motor 111. Keyboard 119 and display means 116 are also provided, in order to program and monitor the proper operation of the apparatus. Timer 123, which may be integrated within the body of the microprocessor or microcontroller 112, allows the user to set the desired periods of times for the delivery of each drug. The manual control block 117 enables manual operation of the apparatus, and push button 118 enables to manually advance the motor while loading the apparatus with new drugs, and while replacing the conduits as hereinbefore discussed. Connector 113 enables communication to other apparatuses, and to a central monitoring apparatus. The power supply unit 115 provides power to the apparatus, and comprises a battery or emergency power supply means.

As previously mentioned, the multi-channel switching unit for use with infusion apparatuses according to the invention is very simple to manufacture, maintain and service. The said switching unit eliminates the need for having disposable cassettes, which are expensive and complicated to maintain, or the need for having a plurality of infusion pumps, which significantly add to the cost of the apparatus. Further, the invention provides significantly improved sterilization and a more reliable apparatus, due to the elimination of several complicated components. The invention further provides an apparatus in which the drug passes from the drug vials to the patient in one disposable continuous conduit.

While preferred embodiments of the invention have been described by way of illustration, it will be understood that the invention may be carried out into practice with many variations, modifications and adaptations, without departing from its spirit or exceeding the scope of the claims. In particular, such variations, modifications and adaptations may concern the connection between the specific channels, the placement of the eccentric discs, and the connection between the plurality of said discs and one or more shafts for opening or closing one or more channels at any given time.

What is claimed is:

1. A multi-drug intravenous infusion apparatus comprising:
    a plurality of vials containing drugs to be provided to a patient;
    a fluid container containing a fluid to be mixed with said drugs;
    conduit means for leading drugs from said vials, mixed with fluid from said container, to means for introducing the drugs with said fluid into the patient's body, said conduit means constituting a monolithic exchangeable unit and comprising:
    a. a main section;
    b. a plurality of individual sections, each individual section comprising at least a collapsible portion connected to said vials and to said main section;
    c. a terminal section connected to said main section and to means for introducing the drugs with said fluid from said fluid into the patient's body; and
    d. a fluid section leading fluid from said fluid container to said terminal section:
    a single pump interposed between said individual sections and said terminal section;
    a switching unit comprising a plurality of switches, each switch being associated with one of said individual sections, wherein each switch is capable of either blocking the drug flow in the associated section by exerting pressure to collapse a collapsible segment thereof or allowing said flow by not exerting said pressure; and
    processor means for controlling the operation of said switching unit.

2. An apparatus according to claim 1 wherein the pump is an infusion pump.

3. An apparatus according to claim 2 wherein the infusion pump is a peristaltic infusion pump.

4. An apparatus according to claim 2 wherein the infusion pump is a cassette infusion pump.

5. An apparatus according to claim 2 wherein the infusion pump and the processor means are encased within a single housing.

6. An apparatus according to claim 1 wherein each switch of the switching unit comprises:

a. A rigid body displaceable towards a portion of one of the individual sections of the conduit means, said body having an operative position in which it exerts pressure on the collapsible portion of one of the individual sections of the conduit means and collapses the same and an inoperative position in which it releases said collapsible portion; and b. Means for selectively displacing said rigid means to its operative position to block the drug flow through said individual section, or return it to its inoperative position to allow said drug flow.

7. An apparatus according to claim 6, wherein the means for selectively displacing the rigid means to its operative position or return it to its inoperative position comprises an eccentric disc rotatable between at least a first angular position in which it contacts said rigid means with a portion of its periphery having a minimum radius, and at least a second angular position in which it contacts said rigid means with a portion of its periphery having a maximum radius.

8. An apparatus according to claim 6 wherein the means for displacing the rigid means of the switch is an electromagnet.

9. An apparatus according to claim 6 wherein the means for displacing the rigid means of the switch is a rotated eccentric disc.

10. An apparatus according to claim 1, wherein each switch of the switching unit comprises an eccentric disc rotatable between at least an operative angular position in which it exerts pressure on the collapsible portion of one of the individual sections of the conduit means and collapses the same and at least an inoperative angular position in which it releases said collapsible portion.

11. An apparatus according to claim 1 wherein the switching unit comprises:
    a. A shaft and at least two eccentric rotatable discs spaced apart on said shaft, each disc having at least two angular positions;
    b. Means such as a motor for rotating said shaft;
    c. For each eccentric disc, a body contacting the perimeter of said disc and displaceable by the rotation of said disc towards an individual conduit section to apply pressure to the outer surface thereof, whereby to collapse the same, or being allowed to become displaced away from said conduit whereby to release the same, in order to block or permit flow in it respectively.

12. An apparatus according to claim 11 wherein each eccentric disc defines at least two states while advancing over its full perimeter.

13. An apparatus according to claim 11 wherein the switching unit also comprises at least one position sensor for providing to the control means the current state of the motor, and/or of the eccentric discs.

14. An apparatus according to claim 11 wherein the means for rotating the shaft is a motor.

15. An apparatus according to claim 14 wherein gear means are provided between the shaft and the motor.

16. An apparatus according to claim 1 wherein at the most, two drugs are provided to the patient at any given time.

17. An apparatus according to claim 1, wherein the control means is a local processor, and wherein keyboard and display means are provided, in order to program the apparatus to timely perform tasks.

18. An apparatus according to claim 1 wherein means are also provided for connecting the apparatus to other infusion apparatuses, and/or to a central control unit which controls plurality of infusion apparatuses.

19. An apparatus according to claim 1 further comprising means for manually advancing the motor in order to allow the replacement of drug vials and conduits position.

20. An apparatus according to claim 1 wherein each switch of the switching unit comprises:
   a. A rotatable eccentric disc having an operative position in which the perimeter of the disc is in contact and exerts pressure on a collapsible portion of one of the individual sections of the conduit means and collapses the same, and an inoperative position in which it is not in contact with said portion and said collapsible portion is released.
   b. Means for angularly rotating said eccentric disc to its operative angular position to block the drug flow through said individual section, or return it to its angular inoperative position to allow said drug flow.

21. An apparatus according to claim 1 wherein the switching unit and the processor means are encased within a housing.

22. An apparatus according to claim 1 wherein the processor means is an external Personal Computer (PC).

* * * * *